(12) United States Patent
Lyttle et al.

(10) Patent No.: US 8,933,130 B2
(45) Date of Patent: Jan. 13, 2015

(54) TREATMENT OF VASOMOTOR SYMPTOMS WITH SELECTIVE ESTROGEN RECEPTOR MODULATORS

(75) Inventors: C. Richard Lyttle, Bala Cynwyd, PA (US); Bart Henderson, Belmont, MA (US); Gary Hattersley, Stow, MA (US)

(73) Assignee: Radius Health, Inc., Cambridge, MA (US)

( * ) Notice: Subject to any disclaimer, the term of this patent is extended or adjusted under 35 U.S.C. 154(b) by 1580 days.

(21) Appl. No.: 12/308,640

(22) PCT Filed: Jun. 22, 2007

(86) PCT No.: PCT/US2007/014598
§ 371 (c)(1),
(2), (4) Date: Oct. 27, 2009

(87) PCT Pub. No.: WO2008/002490
PCT Pub. Date: Jan. 3, 2008

(65) Prior Publication Data
US 2010/0105733 A1    Apr. 29, 2010

Related U.S. Application Data

(60) Provisional application No. 60/816,191, filed on Jun. 23, 2006.

(51) Int. Cl.
*A61K 31/136* (2006.01)
*A61K 31/135* (2006.01)

(52) U.S. Cl.
CPC ................................ *A61K 31/136* (2013.01)
USPC ........................... 514/649; 514/646; 514/579

(58) Field of Classification Search
None
See application file for complete search history.

(56) References Cited

U.S. PATENT DOCUMENTS

| | | | |
|---|---|---|---|
| 7,612,114 B2 | 11/2009 | Hamaoka et al. | |
| 7,960,412 B2 | 6/2011 | Hamaoka et al. | |
| 8,399,520 B2 | 3/2013 | Hamaoka et al. | |
| 2003/0065008 A1 * | 4/2003 | Labrie | ........................ 514/311 |
| 2003/0143276 A1 | 7/2003 | Hsia et al. | |
| 2004/0210080 A1 | 10/2004 | Meng et al. | |
| 2006/0116364 A1 | 6/2006 | Hamaoka et al. | |
| 2007/0155664 A1 | 7/2007 | Ranklove et al. | |
| 2008/0114048 A1 | 5/2008 | Sui et al. | |
| 2009/0325930 A1 | 12/2009 | Hamaoka et al. | |
| 2010/0105733 A1 | 4/2010 | Lyttle et al. | |
| 2011/0124617 A1 | 5/2011 | Lyttle et al. | |
| 2013/0053448 A1 | 2/2013 | O'Dea et al. | |

FOREIGN PATENT DOCUMENTS

| | | | |
|---|---|---|---|
| WO | WO 01/49673 A2 | 7/2001 | |
| WO | WO 03/063859 A1 | 8/2003 | |
| WO | WO 03/091239 A1 | 11/2003 | |
| WO | WO 03/099292 A1 | 12/2003 | |
| WO | WO 2004058682 A1 * | 7/2004 | ............ C07C 215/74 |
| WO | WO 2005/073204 A1 | 8/2005 | |
| WO | WO 2008/002490 A2 | 1/2008 | |
| WO | WO 2009/137104 A1 | 11/2009 | |
| WO | WO 2011/143469 A1 | 11/2011 | |

OTHER PUBLICATIONS

Loprinzi, C.L., et al., "Management of Hot Flashes in Breast-Cancer Survivors," *Lancet Oncol.*, 2:199-204 (2001).
Pandya, K.J., et al., "Pilot Study Using Gabapentin for Tamoxifen-Induced Hot Flashes in Women with Breast Cancer," *Breast Cancer Research and Treatment*, 83;87-89 (2004).
Stearns, V., et al., "A Pilot Trial Assessing the Efficacy of Paroxetine Hydrochloride (Paxil®) in Controlling Hot Flashes in Breast Cancer Survivors," *Annals of Oncology*, 11:17-22 (2000).
Notification of Transmittal of the International Search Report and the Written Opinion of the International Searching Authority, or the Declaration, International Application No. PCT/US2009/002885, Date of Mailing: Sep. 10, 2009.
Notification Concerning Transmittal of International Preliminary Report on Patentability, International Application No. PCT/US2009/002885, Date of Mailing: Nov. 18, 2010.
Notification of Transmittal of the International Search Report and the Written Opinion of the International Searching Authority, or the Declaration, International Application No. PCT/US11/36311, Date of Mailing: Aug. 12, 2011.
Notification Concerning Transmittal of International Preliminary Report on Patentability, Application No. PCT/US2007/014598, date of mailing Jan. 15, 2009.
Office Action, EP 07 796 378.3, dated Sep. 4, 2009.
International Search Report from International Application No. PCT/US2007/014598, Mar. 28, 2008.
Arun, B., et al., "The Search for the Ideal SERM," *Expert. Opin. Pharmacother.*, 3(6):681-691 (2002).
Office Action for U.S. Appl. No. 12/991,791, Mailed on Aug. 15, 2012.
Notification Concerning Transmittal of International Preliminary Report on Patentability, International Application No. PCT/US2011/036311; Mailed on Nov. 22, 2012.
Notice of Allowance, U.S. Appl. No. 13/697,230, Dated: Feb. 20, 2014.

* cited by examiner

*Primary Examiner* — Theodore R West
(74) *Attorney, Agent, or Firm* — Perkins Coie LLP; Michael Wise; Yingli Wang (57) ABSTRACT

The present invention is directed toward methods for treating vasomotor symptoms, (e.g., hot flashes and night sweats) in a patient in need thereof comprising administering a SERM as described herein.

7 Claims, 3 Drawing Sheets

TREATMENT OF VASOMOTOR SYMPTOMS WITH SELECTIVE ESTROGEN RECEPTOR MODULATORS

RELATED APPLICATION

This application is the U.S. National Stage of International Application No. PCT/TUS2007/014598, filed Jun. 22, 2007, published in English, and claims the benefit of U.S. Provisional Application No. 60/816,191, filed on Jun. 23, 2006. The entire teachings of the above application are incorporated herein by reference.

BACKGROUND OF THE INVENTION

Menopausal symptoms (e.g., vasomotor symptoms, loss of libido, sleep disturbances and nausea) are experienced by many pre-, peri- and post-menopausal women. Vasomotor symptoms (e.g., hot flashes and night sweats) are believed to arise due to decreases in estrogen production most commonly associated with natural or surgically induced menopause.

Hot flashes are sudden, intense, hot feelings on the face and upper body and are accompanied by differing degrees of flushing, palpitations, anxiety, irritability, sleep disturbances, and sweating. While the cause of hot flashes associated with vasomotor symptoms has not yet been fully elucidated, it has been hypothesized that hot flashes result from the brain's response to diminished hormones or hormonal fluctuations associated with the menopausal transition. (See e.g. Utian, *Health and Quality of Life Outcomes*, 2005, 3:47.)

Hot flashes affect each woman differently and typically last for a few minutes but can last for up to ten minutes or more in severe cases. Symptoms associated with hot flashes can range from mild to severe, with severe symptoms significantly interfering with a woman's daily life. Vasomotor symptoms can also arise as a result of treatments, such as treatment for breast cancer, that utilize antiestrogen therapy, result in chemo-therapy induced menopause, or that utilize compounds that modulate the estrogen receptor. While vasomotor symptoms mainly affect women, men can also suffer from vasomotor symptoms. For example, men undergoing treatment for prostate cancer and benign prostatic hyperplasia (BPH) can experience hot flashes.

Hot flashes are associated with natural, surgical, transient and iatrogenic menopause also a common symptom for women undergoing treatment for breast cancer. (See e.g. Pandya, *Lancet*, 2005, 366: 818-24.)

Vasomotor symptoms (e.g., hot flashes and night sweats) have traditionally been treated using hormone replacement therapy (HRT). However, the discovery that HRT can cause significant side effects has resulted in a reluctance to utilize HRT for treatment of conditions related to decreases in estrogen production. These side effects, including an increased risk of cardiovascular disease and uterine or breast cancer, are thought to be the result of undesirable estrogen activity in the relevant tissue.

None of the treatments for vasomotor symptoms, including hot flashes, have been completely effective. Thus there exists a need for more effective treatments, including treatment, of vasomotor symptoms such as hot flashes and night sweats, without the sides effects associated with hormone replacement therapy.

SUMMARY OF THE INVENTION

The present invention is directed toward a method of treating vasomotor symptoms in a patient in need thereof comprising administering an effective amount of a selective estrogen receptor modulator (SERM) represented by formula (I), set forth below.

In a particular embodiment, the present invention is directed toward a method of treating hot flashes in a female patient in need thereof comprising administering an effective amount of (R)-6-{2-{Ethyl[4-(2-ethylaminoethyl)benzyl]amino}-4-methoxyphenyl}-5,6,7,8-tetrahydronaphthalen-2-ol, represented by the following structural formula:

In a more particular embodiment, the patient is a female.

The treatment of vasomotor symptoms with a SERM as described above is advantageous because it can effectively reduce or eliminate symptoms such as hot flashes and night sweats without the undesirable side effects associated with traditional therapies.

DETAILED DESCRIPTION OF THE INVENTION

This invention relates to treating vasomotor symptoms in a patient in need thereof. Vasomotor symptoms can manifest as, for example, hot flashes. Vasomotor symptoms can arise as a result of natural or surgically induced menopause.

More specifically, vasomotor symptoms are symptoms which result from the action of the nerves and muscles that cause the blood vessels to constrict or dilate. As used herein, vasomotor symptoms refers to hot flashes, night sweats, palpitation of the heart rhythm, joint pain and muscular weakness. In a particular embodiment, the vasomotor symptoms are hot flashes and night sweats. In an even more particular embodiment, the vasomotor symptom is hot flashes or night sweats associated with menopause and the patient is a female. In a most particular embodiment, the vasomotor symptom is hot flashes and the patient is a female. In another most particular embodiment, the vasomotor symptoms is night sweats and the patient is a female.

One embodiment of the present invention is directed to a method of treating vasomotor symptoms in a patient in need thereof comprising administering to the patient an effective amount of a compound represented by the following formula (I):

wherein T represents a single bond, a C1-C4 alkylene group which may have a substituent, a C2-C4 alkenylene group which may have a substituent, or a C2-C4 alkynylene group which may have a substituent; ═════ $^{(1-1)}$ formula (I-1) represents a single bond or a double bond;

A represents a single bond, a bivalent 5- to 14-membered heterocyclic group which may have a substituent, a 5- to 14-membered heteroarylene group which may have a substituent, a bivalent C3-C14 carbocyclic group which may have a substituent or a C6-C14 arylene group which may have a substituent;

Y represents a single bond, or —(CH$_2$)$_l$—V—(CH2)$_k$—;

V represents a single bond, —(CR$^f$R$^g$)—, —O—, —S—, —S(=O)—, —SO$_2$—, —SO$_2$NR$^c$—, —NR$^c$SO$_2$—, —C(=O)—, —C(=O)O—, —OC(=O)—, —NR$^c$—, —NR$^c$—C(=O)—, —C(=O)—NR$^c$, —NR$^c$—(=O) O—, —OC(=O)—NR$^c$— (wherein R$^c$ represents a hydrogen atom, a C1-C6 alkyl group which may have a substituent, a C2-C6 alkenyl group which may have a substituent, a C2-C7 acyl group which may have a substituent, a C6-C14 aryl group which may have a substituent, a 5- to 14-membered heteroaryl group which may have a substituent, a C3-C8 cycloalkyl group which may have a substituent, or a 5- to 14-membered heterocyclic group which may have a substituent, or, when A is a group other than a single bond, R$^c$ may form, together with A, a 5- to 8-membered ring containing 1 to 2 heteroatoms, R$^f$ and R$^g$ independently represent a hydrogen atom, a hydroxyl group, a halogen atom, a formyl group, a cyano group, a carboxyl group, a C1-C6 alkyl group which may have a substituent, a C2-C6 alkenyl group which may have a substituent, a C1-C6 alkoxy group which may have a substituent, an amino group which may have a substituent, a C1-C6 alkylthio group which may have a substituent, a C3-C8 cycloalkyl group which may have a substituent, a C3-C8 cycloalkyloxy group which may have a substituent, a C3-C8 cycloalkylthio group which may have a substituent, a C6-C14 aryl group which may have a substituent or a 5- to 14-membered heteroaryl group which may have a substituent, and g stands for an integer from 0 to 2), and l and k independently stand for an integer from 0 to 6, the sum of l and k being an integer from 0 to 6;

Z represents —(CH$_2$)$_{l'}$—V'—(CH$_2$)$_{k'}$—;

V' represents a single bond, —(CR$^{f'}$R$^{g'}$)$_{g'}$—, —(CR$^{f'}$R$^{g'}$)$_{g'}$—CH$_2$—O—, —O—, —S—, —S(=O)—, —SO$_2$—, —SO$_2$NR$^{c'}$—, —NR$^{c'}$SO$_2$—, —C(=O)—, —C(=O)— CH$_2$—O—, —C(=O)O—, —OC(=O)—, —NR$^{c'}$—, —NR$^{c'}$—C(=O)—, —C(=O)—NR$^{c'}$—, —NR$^{c'}$—C(=O) O— or —OC(=O)—NR$^{c'}$— (wherein R$^{c'}$ represents a hydrogen atom, a C1-C6 alkyl group which may have a substituent, a C2-C6 alkenyl group which may have a substituent, a C2-C7 acyl group which may have a substituent, a C6-C14 aryl group which may have a substituent, a 5- to 14-membered heteroaryl group which may have a substituent, a C3-C8 cycloalkyl group which may have a substituent, or a 5- to 14-membered heterocyclic group which may have a substituent, R$^{f'}$ and R$^{g'}$ independently represent a hydrogen atom, a hydroxyl group, a halogen atom, a formyl group, a cyano group, a carboxyl group, a C1-C6 alkyl group which may have a substituent, a C2-C6 alkenyl group which may have a substituent, a C1-C6 alkoxy group which may have a substituent, an amino group which may have a substituent, a C1-C6 alkylthio group which may have a substituent, a C3-C8 cycloalkyl group which may have a substituent, a C3-C8 cycloalkyloxy group which may have a substituent, a C3-C8 cycloalkylthio group which may have a substituent, a C6-C14 aryl group which may have a substituent or a 5- to 14-membered heteroaryl group which may have a substituent, or, R$^{f'}$ and R$^{g'}$ may form, with the carbon atoms to which R$^{f'}$ and R$^{g'}$ are bonded, a 5- to 6-membered spiro ring;

g' stands for an integer from 0 to 2; and l' and k' independently stand for an integer from 0 to 6, the sum of l' and k' being an integer from 0 to 6;

ring G represents, together with Q$^1$ and Q$^2$, a phenylene group, a bivalent C5-C6 carbocyclic group, a 5- to 6-membered heteroarylene group or a bivalent 5- to 6-membered heterocyclic group, which may condense with a 5- to 6-membered ring which may have a heteroatom, Q$^1$ and Q$^2$ independently representing a carbon atom or a nitrogen atom;

R$^a$ and R$^b$ are the same as or different from each other and each represents a hydrogen atom, a C1-C6 alkyl group which may have a substituent, a C2-C6 alkenyl group which may have a substituent, a C2-C6 alkynyl group which may have a substituent, a C3-C8 cycloalkyl group which may have a substituent, a C6-C14 aryl group which may have a substituent, a 5- to 14-membered heterocyclic group which may have a substituent, a 5- to 14-membered heteroaryl group which may have a substituent, a C6-C14 arylalkyl group which may have a substituent, a 5- to 14-membered heteroarylalkyl group which may have a substituent, a C1-C6 alkoxy group which may have a substituent or a C2-C7 acyl group which may have a substituent, or when R$^a$ and R$^b$ are bonded together, they may form, together with the nitrogen atom that is adjacent to R$^a$ and R$^b$, a 4- to 10-membered single ring, a double ring, or a spiro ring which may have a substituent, when R$^a$ and/or R$^b$ is bonded to T, they may form, together with the nitrogen atom which R$^a$ and R$^b$ are bonded to, a 5- to 10-membered single ring or double ring which may have a substituent, or, when T, Z, A and Y all represent a single bond, R$^a$ or R$^b$ may be bonded to an atom that forms ring G to form a condensed ring;

W represents a single bond, —(CR$^d$R$^e$)$_f$—CHX—, —CHX—(CR$^d$R$^e$)$_f$—, —CR$^d$X—(CH$_2$)$_q$—, —CR$^d$═CX—, —CX═CR$^d$—, —C═C—, —(CR$^d$R$^e$)$_f$— NX—, —NX—(CR$^d$R$^e$)$_f$—, —NR$^d$—CHX—, —CHX— NR$^d$—, —N═CX—, —CX═N—, —C(=O)—CR$^d$X—, —CR$^d$X—C(=O)—, —C(=O)—NX—, —NX—C (=O)—, —S—CR$^d$X—, —CR$^d$X—S—, —S—NX—, —NX—S—, —O—NX—, —NX—O—, —O—CR$^d$X—, —CR$^d$X—O— or any group from the group represented by the groups having the following formula;

$R^d$ and $R^e$ have the same meaning as defined by $R^f$ and $R^g$, respectively;

X represents a hydrogen atom, a hydroxyl group, a halogen atom, a formyl group, a cyano group, a carboxyl group, a C1-C6 alkyl group which may have a substituent, a C2-C6 alkenyl group which may have a substituent, a C1-C6 alkoxy group which may have a substituent, an amino group which may have a substituent, a C1-C6 alkylthio group which may have a substituent, a C3-C8 cycloalkyl group which may have a substituent, a C3-C8 cycloalkyloxy group which may have a substituent, a C3-C8 cycloalkylthio group which may have a substituent, a C6-C14 aryl group which may have a substituent, or a 5- to 14-membered heteroaryl group which may have a substituent, f has the same meaning as defined by g, and q stands for an integer from 0 to 4, or a group having the following formula;

R' represents 1 to 4 independent hydrogen atoms, oxygen atoms, sulphur atoms, hydroxyl groups (that may be further protected by a protecting group), halogen atoms, formyl groups, cyano groups, carboxyl groups, carbamoyl groups, C1-C6 alkyl groups which may have a substituent, C2-C6 alkenyl groups which may have a substituent, C1-C6 alkoxy groups which may have a substituent, amino groups which may have a substituent, C1-C6 alkylthio groups which may have a substituent, C3-C8 cycloalkyl groups which may have a substituent, C3-C8 cycloalkyloxy groups which may have a substituent, C2-C7 alkylcarbonyloxy groups which may have a substituent, C2-C7 acyl groups which may have a substituent, C3-C8 cycloalkylthio groups which may have a substituent, C6-C14 aryl groups which may have a substituent or 5- to 14-membered heteroaryl groups which may have a substituent, or when R' is in the number of 2 to 4, R' may be bonded to one another to form a 5- to 8-membered ring which may have a substituent, or when W represents any one selected from the group consisting of —(CR$^d$R$^e$)$_f$—CHX—, —CHX—(CR$^d$R$^e$)$_f$—, —CR$^d$=CX—, —CX=CR$^d$—, —(CR$^d$R$^e$)$_f$—NX—, —NX—CR$^d$R$^e$)$_f$—, —NR$^d$—CHX—, —CHX—NR$^d$—, —N=CX—, —CX=N—, —C(=O)—CR$^d$X—, —CR$^d$X—C(=O)—, —C(=O)—NX—, —NX—C(=O)—, —S—CR$^d$X—, —CR$^d$X—S—, —S—NX—, —NX—S—, —O—NX—, —NX—O—, —O—CR$^d$X—, —CR$^d$X—O— or —CR$^x$—, R' may form, together with X, a 5- to 8-membered ring, that may contain 1 to 2 heteroatoms, which may have a substituent;

R" represents 1 to 4 independent hydrogen atoms, hydroxyl groups (that may be further protected by a protecting group), halogen atoms, formyl groups, cyano groups, carboxyl groups, carbamoyl groups, C1-C6 alkyl groups which may have a substituent, C2-C6 alkenyl groups which may have a substituent, C1-C6 alkoxy groups which may have a substituent, amino groups which may have a substituent, C2-C7 acyl groups which may have a substituent, C1-C6 alkylthio groups which may have a substituent, C3-C8 cycloalkyl groups which may have a substituent, C3-C8 cycloalkyloxy groups which may have a substituent, C2-C7 alkylcarbonyloxy groups which may have a substituent, C3-C8 cycloalkylthio groups which may have a substituent, C6-C14 aryl groups which may have a substituent or a 5- to 14-membered heteroaryl groups which may have a substituent, or when R" is in the number of 2 to 4, R" may be bonded to one another to form a 5- to 8-membered ring which may have a substituent;

R represents a hydrogen atom, a hydroxyl group, a halogen atom, a formyl group, a cyano group, a carboxyl group, a carbamoyl group, a C1-C6 alkyl group which may have a substituent, a C2-C6 alkenyl group which may have a substituent, a C1-C6 alkoxy group which may have a substituent, an amino group which may have a substituent, a C2-C7 acyl group which may have a substituent, a C1-C6 alkylthio group which may have a substituent, a C3-C8 cycloalkyl group which may have a substituent, a C3-C8 cycloalkyloxy group which may have a substituent, a C2-C7 alkylcarbonyloxy group which may have a substituent, a C3-C8 cycloalkylthio group which may have a substituent, a C6-C14 aryl group which may have a substituent or a 5- to 14-membered heteroaryl group which may have a substituent, or when W represents —(CR$^d$R$^e$)$_f$—CHX—, —CHX—(CR$^d$R$^e$)$_f$—, —CR$^d$=CX—, —CX=CR$^d$—, —(CR$^d$R$^e$)$_f$—NX—, —NX—(CR$^d$R$^e$)$_f$—, —R$^d$—CHX—, —CHX—NR$^d$—, —N=CX—, —CX=N—, —C(=O)—CR$^d$X—, —CR$^d$X—C(=O), —C(=O)—NX—, —NX—C(=O)—, —S—CR$^d$X—, —CR$^d$X—S—, —S—NX—, —NX—S—, —O—NX—, —NX—O—, —O—CR$^d$X—, —CR$^d$X—O— or —CR$^x$—, R may form, together with X, a 5- to 7-membered ring, that may contain 1 to 2 heteroatoms, which may have a substituent;

L represents a single bond, a C1-C4 alkylene group that may have a substituent, a C2-C4 alkenylene group which may have a substituent, or a C2-C4 alkynylene group which may have a substituent or a salt thereof, or a hydrate thereof.

In another embodiment, the present invention is directed to a method of treating or vasomotor symptoms in a patient in need thereof comprising administering to the patient an effective amount of a compound having the following formula:

wherein

T-Z represents a C1-C4 alkylene group, or —CR$^f$R$^{g'}$—CH$_2$—O— (wherein R$^f$ and R$^{g'}$ independently represent a C1-C6 alkyl group);

A represents a 5- to 14-membered heteroarylene group which may have a substituent or a C6-C14 arylene group which may have a substituent;

Y represents —CH$_2$—NR$^c$— (wherein R$^c$ represents a C1-C6 alkyl group which may have a substituent);

each of R' independently represents a hydrogen atom or a C1-C6 alkoxy group;

R" represents a hydroxyl group which may be further protected by a protecting group or a C1-C6 alkoxy group which may have a substituent;

R$^a$ and R$^b$ are the same as or different from each other, and each represents a hydrogen atom, a C1-C6 alkyl group which may have a substituent, or a C3-C8 cycloalkyl group which may have a substituent or when R$^a$ and R$^b$ are bonded together, they may form, together with the nitrogen atom that is adjacent to $R^a$ and $R^b$, a 4- to 10-membered single ring which may have a substituent or a salt thereof, or a hydrate thereof.

In yet another embodiment, the present invention is directed to a method of treating vasomotor symptoms in a patient in need thereof comprising administering to the patient an effective amount of a compound having the following formula:

wherein $R^{a'}$ and $R^{b'}$ are the same as or different from each other and each represents a hydrogen atom, a C1-C8 alkyl group which may have a substituent, or where $R^{a'}$ and $R^{b'}$, together with a nitrogen atom that adjacent to $R^{a'}$ and $R^{b'}$, form an optionally substituted 4- to 8-membered single ring, a double ring or a spiro ring, which may have additional heteroatoms besides the N adjacent to $R^{a'}$ and $R^{b'}$;

Z' represents —(CR$^f$R$^{g'}$)$_g$—CH$_2$—V''', —(CR$^f$R$^{g'}$)$_g$—C(=O)—V''', or —(CR$^f$R$^{g'}$)$_g$—C(=S)—V''', wherein V''' is a single bond, O or S, and wherein $R^{f'}$ and $R^{g'}$ independently represent a hydrogen atom or a lower C1-C6 alkyl group, and wherein g represents 0 or 1;

══════ (I-1) formula (I-1) represents a single bond or a double bond;

n is 0 or 1;

Y' is N, S, O or CH;

$R^c$ represents a hydrogen atom or a C1-C6 alkyl group which may have a substituent;

R', for each occurrence, represents a hydrogen atom or a C1-C6 alkoxy group; and m represents 1 or 2 or a salt thereof, or a hydrate thereof.

In yet another embodiment, the present invention is directed to a method of treating vasomotor symptoms in a patient in need thereof being comprising administering to the patient an effective amount of a compound having the following formula:

wherein $R^{a'}$ and $R^{b'}$ are the same as or different from each other and each represents a hydrogen atom, a C1-C8 alkyl group which may have a substituent, or where $R^{a'}$ and $R^{b'}$ together with a nitrogen atom that adjacent to $R^{a'}$ and $R^{b'}$, form an optionally substituted 4- to 8-membered single ring, a double ring or a spiro ring, which may have additional heteroatoms besides the N adjacent to $R^{a'}$ and $R^{b'}$;

Z' represents —(CR$^f$R$^{g'}$)$_g$—CH$_2$—V''', —(CR$^f$R$^{g'}$)$_g$—C(=O)—V''', or —(CR$^f$R$^{g'}$)$_g$—C(=S)—V''', wherein V''' is a single bond, O or S, and wherein $R^{f'}$ and $R^{g'}$ independently represent a hydrogen atom or a C1-C6 alkyl group, and wherein g represents 0 or 1;

══════ (I-1) formula (I-1) represents a single bond or a double bond;

n is 0 or 1;

Y' is N, S, O or CH;

$R^c$ represents a hydrogen atom or a C1-C6 alkyl group which may have a substituent;

R', for each occurrence, represents a hydrogen atom or a C1-C6 alkoxy group; and m represents 1 or 2 or a salt thereof, or a hydrate thereof.

In a first particular embodiment, Z' represents —(CR$^f$R$^{g'}$)$_g$—CH$_2$— wherein g represents 1; Y' represents N; and n represents 1. More particularly, $R^{f'}$ and $R^{g'}$ independently represent a hydrogen atom. Even more particularly, $R^c$ represents a C1-C6 alkyl or hydroxy C1-C6 alkyl. Even more preferably $R^{a'}$ and $R^{b'}$ independently represent a hydrogen atom or a C1-C8 alkyl. Most particularly, $R^c$ represents Et and R' represents —OMe. In another even more particular embodiment, $R^{a'}$ and $R^{b'}$, together, with the nitrogen atom adjacent to $R^{a'}$ and $R^{b'}$, form a partial structure selected from the group consisting of the following structures:

Most particularly, $R^c$ represents Et and R' represents —OMe.

In a second particular, embodiment, Z' represents —(CR$^f$R$^{g'}$)$_g$—CH$_2$—O, wherein g represents 1. Even more particularly, $R^c$ represents a C1-C6 alkyl or hydroxy C1-C6 alkyl. Even more particularly, $R^{a'}$ and $R^{b'}$ independently represent a hydrogen atom or a C1-C8 alkyl. Most particularly, $R^c$ represents —(CH$_2$)$_2$OH and R' represents —OMe. In another even more particular embodiment, $R^a$ and $R^b$, together, with the nitrogen atom adjacent to $R^a$ and $R^b$, form a partial structure selected from the group consisting of the following structures:

Most particularly, $R^c$ represents HO(CH$_2$)$_2$— and R' represents —OMe.

In another particular embodiment, the present invention is directed to a method of treating vasomotor symptoms in a patient in need thereof comprising administering to the patient an effective amount of a compound having the following formula:

wherein $R^{a'}$ and $R^{b'}$ independently represent a hydrogen atom, a C1-C8 alkyl group, or $R^{a'}$ and $R^{b'}$, together with the nitrogen atom adjacent to $R^{a'}$ and $R^{b'}$, form a 4- to 8-membered ring, which may have an additional heteroatom besides the nitrogen atom adjacent to $R^{a'}$ and $R^{b'}$;

$R^c$ represents a hydrogen atom or a C1-C6 alkyl group or a hydroxy C1-C6 alkyl group or a salt thereof, or a hydrate thereof.

In a particular embodiment, $R^{a'}$ and $R^{b'}$, together with the nitrogen atom adjacent to $R^{a'}$ and $R^{b'}$, form a partial structure selected from the group consisting of the following structures:

More particularly, $R^c$ is a hydrogen atom or a C1-C6 alkyl group. Even more preferably, $R^c$ is an ethyl group.

In another particular embodiment, $R^{a'}$ and $R^{b'}$ independently represent a hydrogen atom, a C1-C8 alkyl group. More preferably, $R^c$ is a hydrogen atom or a C1-C6 alkyl group. Even more preferably, $R^c$ is an ethyl group.

Examples of specific compounds for use in the method described herein are set forth below:

(R)-6-(2-(N-(4-(2-(ethylamino)ethyl)benzyl)-N-ethylamino)-4,5-dimethoxyphenyl)-5,6,7,8-tetrahydronaphthalen-2-ol (R)-6-{2-{Ethyl[4-(2-methylaminoethyl)benzyl]amino}-4-methoxyphenyl}-5,6,7,8-tetrahydronaphthalen-2-ol (R)-6-{2-{[4-(2-Dimethylaminoethoxy)benzyl](2-hydroxyethyl)amino}-4-methoxyphenyl)-5,6,7,8-tetrahydronaphthalen-2-ol

11

(R)-6-{2-{(2-Hydroxyethyl)[4-(2-piperidin-ylethoxy)benzyl]amino}-4-methoxyphenyl}-5,6,7,8-tetrahydronaphthalen-2-ol (R)-6-{2-{(2-Hydroxyethyl) {4-{2-[(2-methoxy-ethyl)methy amino]ethoxy}benzyl}amino}-4-methoxyphenyl}-5,6,7,8-tetrahydronaphthalen-2-ol (R)-6-{2-[[4-(2-Dimethylamino-2-methylpropoxy)benzyl](2-hydroxyethyl)amino]-4-methoxyphenyl)}-5,6,7,8-tetrahydronaphthalen-2-ol

12

(R)-6-{2-{Ethyl[4-(2-propylaminoethyl)benzyl]amino}-4-methoxyphenyl}-5,6,7,8-tetrahydronaphthalen-2-ol

(R)-6-{2-{Ethyl[4-(2-ethylaminoethyl)benzyl]amino}-4,5-dimethoxyphenyl}-5,6,7,8-tetrahydronaphthalen-2-ol

(R)-6-{2-{[4-(2-butylaminoethyl)benzyl]ethylamino}-4-methoxyphenyl}-5,6,7,8-tetrahydronaphthalen-2-ol (R)-6-{2-Ethyl[4-(2-isopropylaminoethyl)benzyl]amino}-4-methoxyphenyl}-5,6,7,8-tetrahydronaphthalen-2-ol (R)-6-{2-{[4-(2-tert-butylaminoethyl)benzyl]ethylamino}-4-methoxyphenyl}-5,6,7,8-tetrahydronaphthalen-2-ol (R)-6-{2-{[4-(2-cyclohexylaminoethyl)benzyl]ethylamino}-4-methoxyphenyl}-5,6,7,8-tetrahydronaphthalen-2-ol A most particular embodiment of the present invention is directed to a method of treating vasomotor symptoms in a patient in need thereof comprising administering to the patient an effective amount of (R)-6-{2-{Ethyl[4-(2-ethylaminoethyl)benzyl]amino}-4-methoxyphenyl}-5,6,7,8-tetrahydronaphthalen-2-ol (hereinafter "SERM A"), a compound having the following formula:

Another most particular embodiment is directed toward a method of treating hot flashes in female patients in need thereof comprising administering an effective amount of (R)-6-{2-{Ethyl[4-(2-ethylaminoethyl)benzyl]amino}-4-methoxyphenyl}-5,6,7,8-tetrahydronaphthalen-2-ol (SERM A) to the female patient.

Figure 1:
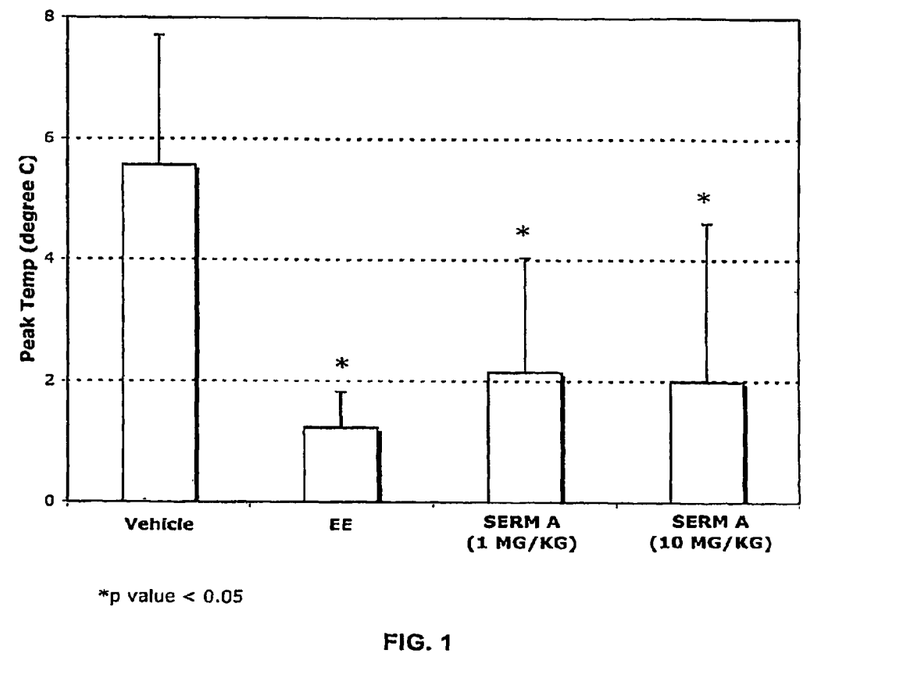
FIG. 1. is a bar graph illustrating the ability of SERM A to modulate vasomotor activity in a rodent model of hot flashes.
Figure 2:
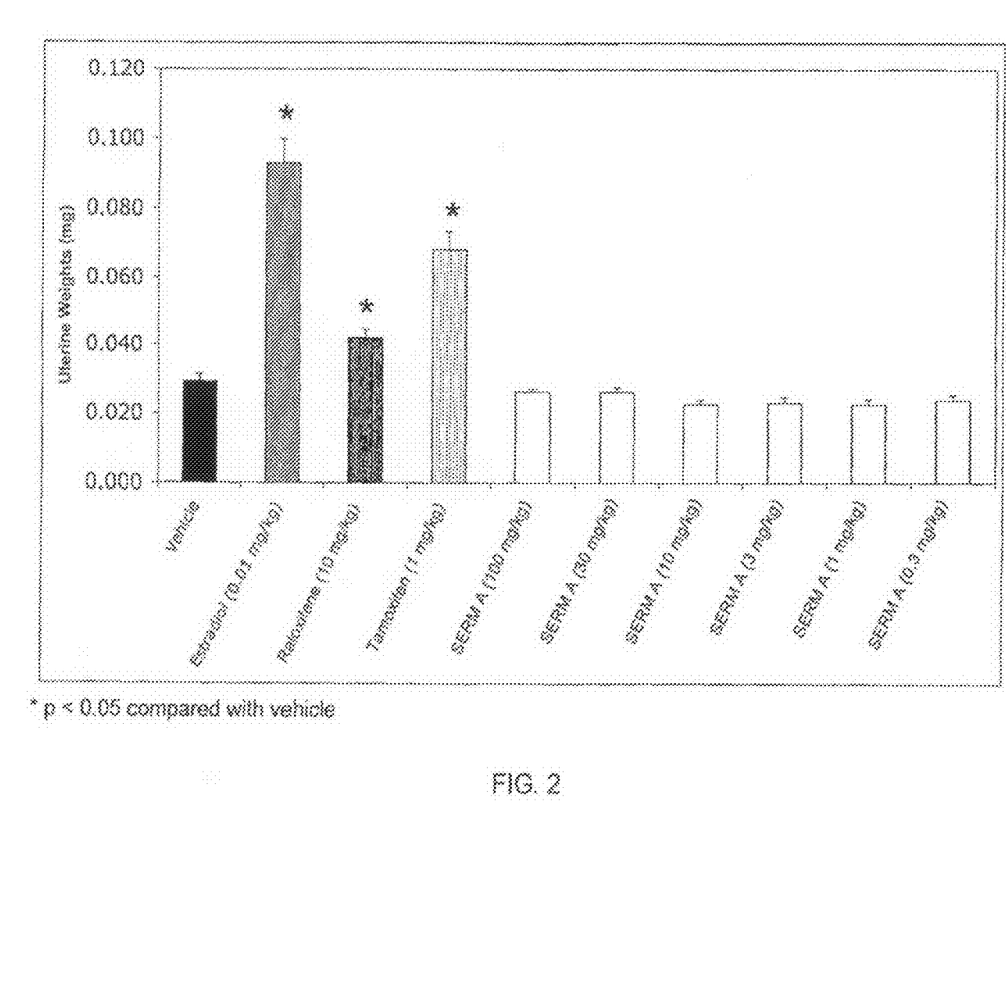
FIG. 2. is a bar graph illustrating tissue selectivity of SERM A.
Figure 3:
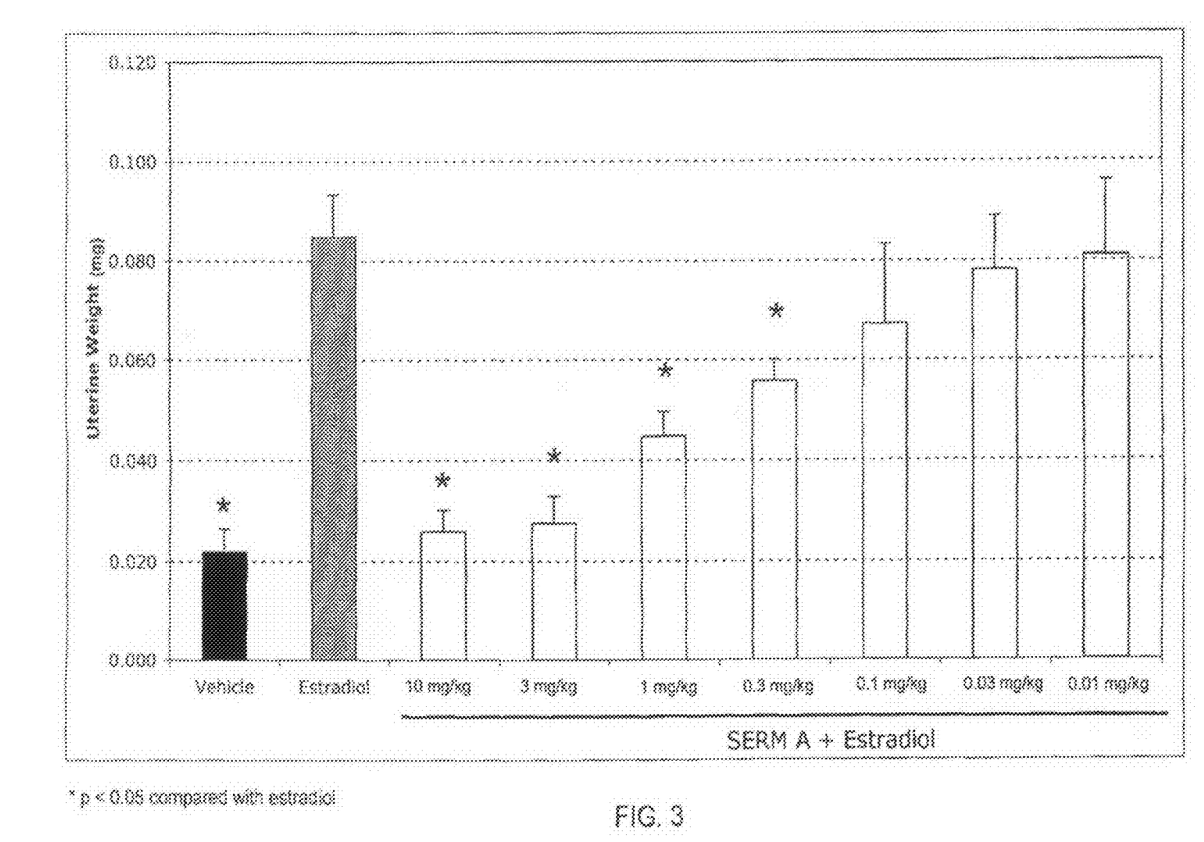
FIG. 3. is a bar graph illustrating antagonism of estradiol mediated uterine stimulation.

SERM A has been found to be active in a rodent model of hot flashes, suppressing the elevation of tail skin temperature associated with morphine addiction withdrawal in morphine-addicted ovariectomized rats. (FIG. 1). Tissue selectivity of SERA has also been demonstrated by the lack of uterine stimulation at doses effective at modulating vasomotor response (FIGS. 2 and 3).

A suitable SERM according to the present invention should be efficacious in treating vasomotor symptoms in a patient. For example, in treating hot flashes, a SERM should eliminate, prevent, or significantly reduce the severity of hot flashes without significantly increasing uterine weight. A more detailed description of the SERMs utilized in the methods of the present invention is included in Hamaoka, et al., U.S. Application Publication No. 2006-0116364A1 (U.S. application Ser. No. 11/158,245), the entire teachings of which are hereby incorporated by reference.

It is believed that efficacious SERMs for the purposes of this invention may act as agonists in the brain tissue of a patient and antagonists in breast tissue. In addition, in symptoms, such as hot flashes, suffered by women, it is believed that suitable SERMS may additionally act as antagonists in uterine and breast tissue.

The SERMs described herein should also be effective in treating and/or preventing additional menopausal symptoms, such as, loss of libido, sleep disturbances, and nausea.

The definition and usage of the terms and the like used in the present specification and claims are as follows:

Although the structural formula of the compound is sometimes described as representing a given isomer for the sake of convenience, the present invention includes all the isomers that may be generated in terms of compound structures, including geometric isomers, optical isomers, stereoisomers, tautomers and the like, and it is not limited to the formula given for the sake of convenience regardless of whether it is a single isomer (for instance, enantiomer) or a mixture of isomers (for instance, racemic mixture).

The term "and/or" is used with the meaning that includes both the "and" case and the "or" case.

The term "halogen atom" used herein means a fluorine atom, a chlorine atom, a bromine atom, an iodine atom and the like, preferably a fluorine atom or a chlorine atom, and more preferably a fluorine atom.

The term "C1-C6 or C1-C8 alkyl group" or a C1-C6 or C1-C8 alkyl group portion in a substituent containing a C1-C6 or C1-C8 alkyl group portion (for instance, C6-C14 arylalkyl group) which are used herein means a linear or a branched alkyl group having 1 to 6 carbons, specifically, examples include methyl group, ethyl group, n-propyl group, iso-propyl group, n-butyl group, iso-butyl group, sec-butyl group, tert-butyl group, n-pentyl group, 1,1-dimethylpropyl group, 1,2-dimethylpropyl group, 2,2-dimethylpropyl group, 1-ethylpropyl group, n-hexyl group, 1-ethyl-2-methylpropyl group, 1,1,2-trimethylpropyl group, 1-ethylbutyl group, 1-methylbutyl group, 2-methylbutyl group, 1,1-dimethylbutyl group, 1,2-dimethylbutyl group, 2,2-dimethylbutyl group, 1,3-dimethylbutyl group, 2,3-dimethylbutyl group, 2-ethylbutyl group, 2-methylpentyl group, 3-methylpentyl group and the like, and preferably methyl group, ethyl group, n-propyl group, iso-propyl group, n-butyl group, iso-butyl group, sec-butyl group, tert-butyl group, n-pentyl group and the like.

The term "C2-C6 alkenyl group" used herein means a linear or a branched alkenyl group with 2 to 6 carbons, specifically, examples include vinyl group, allyl group, 1-propenyl group, isopropenyl group, 2-methyl-1-propenyl group, 2-methyl-2-propenyl group, 1-butenyl group, 2-butenyl group, 3-butenyl group, 1-pentenyl group, 1-hexenyl group, 1,3-hexadienyl group, 1,5-hexadienyl group and the like.

The term "C2-C6 alkynyl group" used herein means a linear or a branched alkynyl group with 2 to 6 carbons, specifically, examples include ethynyl group, 1-propynyl group, 2-propynyl group, 1-butynyl group, 2-butynyl group, 3-butynyl group, 1-ethynyl-2-propynyl group, 1-methyl-2-propynyl group, 1-pentynyl group, 1-hexynyl group, 1,3-hexadiynyl group, 1,5-hexadiynyl group and the like.

The term "alkylene group" used herein means a bivalent group derived by further removing one hydrogen atom at any position from the "alkyl group" defined above, specifically, examples of "C1-C4 alkylene group" include methylene group, ethylene group, methylethylene group, ethylethylene group, 1,1-dimethylethylene group, 1,2-dimethylethylene group, trimethylene group, 1-methyltrimethylene group, 2-methyltrimethylene group, tetramethylene group and the like, and preferably, methylene group, ethylene group, methylethylene group, 1,1-dimethylethylene group, trimethylene group and the like.

The term "alkenylene group" used herein means a bivalent group derived by further removing one hydrogen atom at any position from the "alkenyl group" defined above, specifically, examples of "C2-C4 alkenylene group" include vinylene group, propenylene group, butenylene group and the like, and preferably, vinylene group, propenylene group and butenylene group.

The term "alkynylene group" used herein means a bivalent group derived by further removing one hydrogen atom at any position from the "alkynyl group" defined above, specifically, examples of "C2-C4 alkynylene group" include ethynylene group, propynylene group, butynylene group and the like, and preferably, ethynylene group, propynylene group and butynylene group.

The term "C3-C8 cycloalkyl group" used herein means an aliphatic hydrocarbon cyclic group with 3 to 8 carbon atoms, specifically, examples include cyclopropyl group, cyclobutyl group, cyclopentyl group, cyclohexyl group, cycloheptyl group, cyclooctyl group and the like, and preferably, cyclopropyl group, cyclobutyl group, cyclopentyl group and cyclohexyl group.

The term "C1-C6 alkoxy group" used herein means an oxy group to which the "C1-C6 alkyl group" defined above is bonded, specifically, examples include methoxy group, ethoxy group, n-propoxy group, iso-propoxy group, n-butoxy group, iso-butoxy group, sec-butoxy group, tert-butoxy group, n-pentyloxy group, iso-pentyloxy group, sec-pentyloxy group, n-hexyloxy group, iso-hexyloxy group, 1,1-dimethylpropoxy group, 1,2-dimethylpropoxy group, 2,2-dimethylpropoxy group, 2-methylbutoxy group, 1-ethyl-2-methylpropoxy group, 1,1,2-trimethylpropoxy group, 1,1-dimethylbutoxy group, 1,2-dimethylbutoxy group, 2,2-dimethylbutoxy group, 2,3-dimethylbutoxy group, 1,3-dimethylbutoxy group, 2-ethylbutoxy group, 2-methylpentyloxy group, 3-methylpentyloxy group and the like, preferably methoxy group, ethoxy group, n-propoxy group and iso-propoxy group, and more preferably, methoxy group and ethoxy group.

The term "C3-C8 cycloalkyloxy group" used herein means an oxy group to which the "C3-C8 cycloalkyl group" defined above is bonded, specifically, examples include cyclopropoxy group, cyclobutoxy group, cyclopentyloxy group, cyclohexyloxy group, cycloheptyloxy group, cyclooctyloxy group and the like, and preferably, cyclopropyloxy group, cyclobutyloxy group and cyclopentyloxy group.

The term "C2-C7 acyl group" used herein means a carbonyl group to which the "C1-C6 alkyl group" defined above is bonded, specifically, examples include acetyl group, propionyl group, butyryl group, isobutyryl group, valeryl group, isovaleryl group, pivaloyl group and the like, and preferably, acetyl group, propionyl group, butyryl group, isobutyryl group, valeryl group, isovaleryl group and pivaloyl group.

The term "C1-C6 alkylthio group" used herein means a thio group to which the "C1-C6 alkyl group" defined above is bonded, specifically, examples include methylthio group, ethylthio group, n-propylthio group, iso-propylthio group, n-butylthio group, iso-butylthio group, sec-butylthio group, tert-butylthio group, n-pentylthio group, 1,1-dimethylpropylthio group, 1,2-dimethylpropylthio group, 2,2-dimethylpropylthio group, 1-ethylpropylthio group, n-hexylthio group, 1-ethyl-2-methylpropylthio group, 1,1,2-trimethylpropylthio group, 1-ethylbutylthio group, 1-methylbutylthio group, 2-methylbutylthio group, 1,1-dimethylbutylthio group, 1,2-dimethylbutylthio group, 2,2-dimethylbutylthio group, 1,3-dimethylbutylthio group, 2,3-dimethylbutylthio group, 2-ethylbutylthio group, 2-methylpentylthio group, 3-methylpentylthio group and the like.

The term "C3-C8 cycloalkylthio group" used herein means a thio group to which the "C3-C8 cycloalkyl group" defined above is bonded, specifically, examples include cyclopropylthio group, cyclobutylthio group, cyclopentylthio group, cyclohexylthio group, cycloheptylthio group, or cyclooctylthio group and the like, and preferably, cyclopropylthio group, cyclobutylthio group and cyclopentylthio group.

The term "C3-C14 carbocyclic group" used herein means a monovalent or a bivalent cyclic group which is a saturated, partially saturated or unsaturated and which is formed by 3 to 14 carbon atoms, containing the a C3-C8 cycloalkyl group described above and a C5-C6 carbocyclic group described below. Specific examples of this group include C3-C8 cycloalkenyl groups such as cyclopropenyl, cyclobutenyl, 1,3-cyclobutadienyl, cyclopentenyl, 1,3-cyclopentadienyl, cyclohexenyl, 1,3-cyclohexadienyl and 1,4-cyclohexadienyl, a bicyclic or tricyclic C9-C14 ring group which is saturated, partially saturated or unsaturated, such as decahydronaphthyl group, octahydroindenyl group, tetradecahydroanthracenyl group, tetrahydrophenanthrenyl group, octahydronaphthyl group and hexahydroindenyl group and the like, as well as bivalent groups corresponding thereto, preferably, C3-C8 cycloalkyl group.

The term "C6-C14 aryl group" used herein means an aryl group formed by 6 to 14 carbon atoms containing a monocyclic ring group, or a condensed ring group such as a bicyclic or a tricyclic ring group. Specific examples of this group include phenyl group, indenyl group, naphthyl group, azulenyl group, heptalenyl group, biphenyl group, indacenyl group, acenaphthylenyl group, fluorenyl group, phenalenyl group, phenanthrenyl group, anthracenyl group, cyclopentacyclooctenyl group or benzocyclooctenyl group and the like. The preferred "C6-C14 aryl group" is C6-C10 aryl group, that is to say, phenyl group, naphthyl group or indenyl group.

The term "C6-C14 arylene group" used herein means a bivalent group derived by further removing one hydrogen atom from the C6-C14 aryl group described above.

The term "5- to 14-membered heteroaryl group" used herein means a monocyclic, bicyclic or tricyclic heteroaryl group, whose number of atoms forming the ring is 5 to 14, and containing not less than one heteroatom from not less than one species selected from the group consisting of a nitrogen atom, a sulfur atom, and an oxygen atom, and containing 5- to 6-membered heteroaryl groups described below. Specific examples of this group include, 1) for instance, pyrrolyl group, pyridyl group, pyridazinyl group, pyrimidinyl group, pyrazinyl group, triazolyl group, tetrazolyl group, benzotriazolyl group, pyrazolyl group, imidazolyl group, benzimidazolyl group, indolyl group, isoindolyl group, indolizinyl group, purinyl group, indazolyl group, quinolyl group, isoquinolyl group, quinolizinyl group, phthalazyl group, naphthylidinyl group, quinoxalinyl group, quinazolinyl group, cinnolinyl group, pteridinyl group, imidazotriazinyl group, pyrazinopyridazinyl group, acridinyl group, phenanthridinyl group, carbazolyl group, perimidinyl group, phenanthrolinyl group, phenazinyl group, imidazopyridinyl group, imidazopyrimidinyl group, pyrazolopyridinyl group and the like as a nitrogen-containing heteroaryl group; 2) thienyl group, benzothienyl group and the like as a sulfur-containing heteroaryl group; 3) furyl group, pyranyl group, benzofuryl group, isobenzofuryl group and the like as an oxygen-containing heteroaryl group; 4) thiazolyl group, isothiazolyl group, benzothiazolyl group, benzothiaziazolyl group, phenothiazinyl group, isoxazolyl group, furazanyl group, phenoxazinyl group, oxazolyl group, benzooxazolyl group, oxadiazolyl group, pyrazolooxazolyl group, imidazothiazolyl group, thienofuranyl group, furopyrrolyl group, pyridooxazinyl group and the like as a heteroaryl group whose structure contains not less than two different species of heteroatoms. A 5- to 10-membered heteroaryl group is preferable, that is to say, a monocyclic or a bicyclic heteroaryl group whose number of atoms forming the ring of the cyclic group is 5 to 10, containing not less than one heteroatom among the atoms forming the ring of the cyclic group. Specific examples of this group include 1) for instance, pyrrolyl group, pyridyl group, pyridazinyl group, pyrimidinyl group, pyrazinyl group, triazolyl group, tetrazolyl group, benzotriazolyl group, pyrazolyl group, imidazolyl group, benzimidazolyl group, indolyl group, isoindolyl group, indolizinyl group, purinyl group, indazolyl group, quinolyl group, isoquinolyl group, quinolizinyl group, phthalazyl group, naphthylidinyl group, quinoxalinyl group, quinazolinyl group, cinnolinyl group, pteridinyl group, imidazotriazinyl group, pyrazinopyridazinyl group, imidazopyridinyl group, imidazopyrimidinyl group, pyrazolopyridinyl group and the like as a nitrogen-containing heteroaryl group; 2) thienyl group, benzothienyl group and the like as a sulfur-containing heteroaryl group; 3) furyl group, pyranyl group, benzofuryl group, isobenzofuryl group and the like as an oxygen-containing heteroaryl group; 4) thiazolyl group, isothiazolyl group, benzothiazolyl group, benzothiaziazolyl group, isoxazolyl group, furazanyl group, oxazolyl group, benzooxazolyl group, oxadiazolyl group, pyrazolooxazolyl group, imidazothiazolyl group, thienofuranyl group, furopyrrolyl group, pyridooxazinyl group and the like as a heteroaryl group whose structure contains not less than two different species of heteroatoms.

Pyrrolyl group, furyl group, thienyl group, pyridyl group, benzothienyl group, benzofuryl group, indolyl group, benzyl group and indazolyl group are more preferred.

The term "5- to 14-membered heteroarylene group" used herein means a bivalent group which is derived by further removing one hydrogen atom from the 5- to 14-membered heteroaryl group described above, and which contains 5- to 6-membered heteroarylene group described below.

The term "5- to 14-membered heterocyclic group" used herein means a group:
1) whose number of atoms forming the ring of the cyclic group is 5 to 14;
2) containing not less than one heteroatom from not less than one species selected from the group consisting of a nitrogen atom, a sulfur atom and an oxygen atom among the atoms forming the ring of the cyclic group;
3) that may contain 1 to 3 carbonyl groups in the ring;
4) that is monovalent or bivalent;
5) that may be non-aromatic monocyclic, bicyclic or tricyclic heterocyclic, and containing a 5- to 6-membered heterocyclic group described below. Specific examples of this group include pyrrolidinyl group, pyrrolyl group, piperidyl group, piperidino group, piperazinyl group, imidazolyl group, pirazolidinyl group, imidazolidinyl group, morpholinyl group, morpholino group, tetrahydrofuryl group, tetrahydropyranyl group and the like, as well as the bivalent groups corresponding thereto, as well as groups derived from pyridone ring and non-aromatic condensed ring groups (groups derived from, for instance, phthalimide ring, succinimide ring and the like). Pyrrolidinyl group, pyrrolinyl group, piperidyl group, piperazinyl group, imidazolinyl group, pirazolidinyl group, imidazolidinyl group, morpholinyl group, tetrahydrofuryl group, tetrahydropyranyl group, aziridinyl group and the like are preferred.

The term "5- to 6-membered heteroaryl group" used herein means a monocyclic heteroaryl group, whose number of atoms forming the ring is 5 to 6, and containing 1 to 3 heteroatoms of not less than one species selected from the group consisting of a nitrogen atom, a sulfur atom and an oxygen atom, among the atoms forming the ring. Examples include pyrrolyl group, imidazolyl group, pyrazolyl group, triazolyl group, pyridyl group, pyridazinyl group, pyrimidinyl group, pyrazinyl group, triazinyl group, furyl group, thienyl group, thiazolyl group, oxazolyl group, isoxazolyl group and the like, the term "heteroaryl group" herein also includes pyridonyl group that may have a substituent on the nitrogen atom. Pyrrolyl group, pyridyl group, pyridonyl group, pyridazinyl group, pyrimidinyl group, pyrazinyl group, furyl group or thienyl group is preferred.

The term "5- to 6-membered heteroarylene group" used herein means a bivalent group derived by further removing one hydrogen atom from the 5- to 6-membered heteroaryl group described above.

The term "5- to 6-membered heterocyclic group" used herein means a monovalent or a bivalent heterocyclic group, whose number of atoms forming the ring is 5 to 6, and containing not less than one heteroatom selected from the group consisting of a nitrogen atom, a sulfur atom and an oxygen atom. Specifically, examples include piperidyl group, piperazinyl group, morpholinyl group, thiomorpholinyl group, tetrahydro-2-pyronyl group, tetrahydropyranyl group, tetrahydrothiopyranyl group, piperidin-2-onyl group, tetrahydrofuranyl group, tetrahydrothyenyl group, pyrrolidinyl group, tetrahydrofuran-2-onyl group, pyrrolidin-2-onyl group, group represented by the following formula:

and the like, as well as bivalent groups corresponding thereto. Preferred examples of this "5- to 6-membered heterocyclic group" include piperidyl group, piperazinyl group, morpholinyl group, thiomorpholinyl group, tetrahydro-2-pyronyl group, tetrahydropyranyl group, tetrahydrothiopyranyl group, piperidine-2-onyl group, group represented by the following formula:

or bivalent groups corresponding thereto.

The term "C5-C6 carbocyclic group" used herein means a monovalent or a bivalent cyclic group formed by 5 to 6 carbon atoms, which may be saturated, partially saturated or unsaturated.

The term "C6-C14 aryl C1-C6 alkoxy group" used herein means a group resulting from the substitution of any hydrogen atom in the C1-C6 alkoxy group by the C6-C14 aryl group, and examples include benzyloxy group and the like.

Representative examples of the substituent as in "may have a substituent" include, in case no other particular expression is given, the group of substituent including:

(1) halogen atoms
(for instance, a fluorine atom, a chlorine atom, a bromine atom, an iodine atom and the like);
(2) hydroxyl groups;
(3) cyano groups;
(4) nitro groups;
(5) carboxyl groups;
(6) oxo groups;
(7) amino groups;
(8) C1-C6 alkyl groups
(for instance, methyl group, ethyl group, n-propyl group, iso-propyl group, n-butyl group, tert-butyl group, n-pentyl group, 1,1-dimethylpropyl group, 1,2-dimethylpropyl group, 2,2-dimethylpropyl group, 1-ethylpropyl group, 2-methylbutyl group, n-hexyl group and the like);
(9) C2-C6 alkenyl groups
(for instance, vinyl group, allyl group, 1-propenyl group, isopropenyl group, 2-methyl-1-propenyl group, 1-butenyl group and the like);
(10) C2-C6 alkynyl groups
(for instance, ethinyl group, 1-propynyl group, 2-propynyl group, 1-butynyl group, 2-butynyl group, 3-butynyl group, 1-ethynyl-2-propynyl group, 1-methyl-2-propynyl group and the like);
(11) C3-C8 cycloalkyl groups
(for instance, cyclopropyl group, cyclobutyl group, cyclopentyl group, cyclohexyl group, cycloheptyl group, cyclooctyl group and the like);
(12) C3-C8 cycloalkenyl groups
(for instance, cyclopropen-1-yl, cyclopropen-3-yl, cyclobuten-1-yl, cyclobuten-3-yl, 1,3-cyclobutadien-1-yl, cyclopenten-1-yl, cyclopenten-3-yl, cyclopenten-4-yl, 1,3-cyclopentadien-1-yl, 1,3-cyclopentadien-2-yl, 1,3-cyclopentadien-5-yl, cyclohexen-1-yl, cyclohexen-3-yl, cyclohexen-4-yl, 1,3-cyclohexadien-1-yl, 1,3-cyclohexadien-2-yl, 1,3-cyclohexadien-5-yl, 1,4-cyclohexadien-3-yl, 1,4-cyclohexadien-1-yl and the like);
(13) C1-C6 alkoxy groups
(for instance, methoxy group, ethoxy group, n-propoxy group, iso-propoxy group, n-butoxy group, iso-butoxy group, sec-butoxy group, tert-butoxy group, n-pentyloxy group, iso-pentyloxy group, sec-pentyloxy group, n-hexyloxy group, iso-hexyloxy group, 1,1-dimethylpropoxy group, 1,2-dimethylpropoxy group, 2,2-dimethylpropoxy group and the like);
(14) C1-C6 alkenyloxy groups (for instance, vinyloxy group, aryloxy group, 1-propenyloxy group, isopropenyloxy group, 2-methyl-1-propenyloxy group, 1-butenyloxy group, 2-butenyloxy group, 3-butenyloxy group, 1-pentenyloxy group, 1-hexenyloxy group, 1,3-hexanedienyloxy group and the like);
(15) C1-C6 alkylthio groups
(for instance, methylthio group, ethylthio group, n-propylthio group, iso-propylthio group, n-butylthio group, iso-butylthio group, sec-butylthio group, tert-butylthio group, n-pentylthio group, 1,1-dimethylpropylthio group, 1,2-dimethylpropylthio group, 2,2-dimethylpropylthio group, 1-ethylpropylthio group, 2-methylbutylthio group, n-hexylthio group, 1,3-dimethylbutylthio group and the like);
(16) C1-C6 alkenylthio groups
(for instance, vinylthio group, allylthio group, 1-propenylthio group, isopropenylthio group, 2-methyl-1-propenylthio group, 2-methyl-2-propenylthio group, 1-butenylthio group, 2-butenylthio group, 3-butenylthio group, 1-pentenylthio group, 1-hexenylthio group, 1,3-hexadienylthio group and the like);
(17) C1-C14 aryloxy groups
(for instance, phenoxy group and the like);
(18) C2-C7 acyl groups
(for instance, acetyl group, propionyl group, butyryl group and the like);
(19) C6-C14 aryl groups
(for instance, phenyl group, 1-naphthyl group, 2-naphthyl group and the like);
(20) 5- to 14-membered heterocyclic groups
(for instance, 1) pyrrolidinyl group, pyrrolinyl group, piperidyl group, piperazinyl group, imidazolinyl group, pirazolidinyl group, imidazolidinyl group, morpholinyl group, tetrahydrofuryl group, tetrahydropyranyl group, aziridinyl group, oxiranyl group and oxathiolanyl group; 2) groups derived from pyridone ring; 3) groups derived from condensed ring such as phthalimide ring and succinimide ring, and the like);
(21) 5- to 14-membered heteroaryl groups
(for instance, pyrrolyl group, pyridyl group, pyridazinyl group, pyrimidinyl group, pyrazinyl group, imidazolyl group, benzimidazolyl group, indolyl group, indazolyl group, quinolyl group, isoquinolyl group, thienyl group, benzothienyl group, furyl group, pyranyl group, benzofuryl group, thiazolyl group, benzothiazolyl group and the like);
(22) carbamoyl groups;
(23) sulfonyl groups having a C1-C6 alkyl group as substituent;
(24) sulfonamide groups;
(25) C1-C6 alkyl carbamoyl groups;
(26) C1-C6 alkoxycarbonyl groups;
(27) C1-C6 alkyl carbonyloxy groups;
(28) C1-C6 alkyl sulfonyl groups;
(29) C1-C6 alkylsulfinyl groups;
(30) formyl groups;
and the like, and "may have a substituent" indicates that 1 to 5 groups of not less than 1 species selected from the substituent group mentioned above may be present as a substituent.

In addition, the amino groups, the C1-C6 alkyl groups, the C2-C6 alkenyl groups, the C2-C6 alkynyl groups, the C3-C8 cycloalkyl groups, the C3-C8 cycloalkenyl groups, the C1-C6 alkoxy groups, the C1-C6 alkenyloxy groups, the C1-C6 alkylthio groups, the C1-C6 alkenylthio groups, the C1-C14 aryloxy groups, the C2-C7 acyl groups, the C6-C14 aryl groups, the 5- to 14-membered heterocyclic groups or the 5- to 14-membered heteroaryl groups, the carbamoyl groups, the sulfonyl groups having a C1-C6 alkyl group as substituent, or the sulfonamide groups of (7) to (24) mentioned above, which are enumerated as the substituent as in "may have a substituent", may be further substituted by 1 to 5 groups selected from the group consisting of:
(a) halogen atoms;
(b) hydroxyl groups;
(c) cyano groups;
(d) nitro groups;
(e) carboxyl groups;
(f) an oxo group;
(g) amino groups;
(h) C1-C6 alkyl groups;
(i) C2-C6 alkenyl groups;
(j) C2-C6 alkynyl groups;
(k) C3-C8 cycloalkyl groups;
(l) C3-C8 cycloalkenyl groups;
(m) C1-C6 alkoxy groups;
(n) C1-C6 alkenyloxy groups;
(o) C1-C6 alkylthio groups;
(p) C1-C6 alkenylthio groups;
(q) C1-C14 aryloxy groups;
(r) C2-C7 acyl groups;
(s) C6-C14 aryl groups;
(t) C5-C14 heterocyclic groups;
(u) 5- to 14-membered heteroaryl groups;
(v) carbamoyl groups;
(w) sulfonyl groups having C1-C6 alkyl group as a substituent; and
(x) sulfonamide groups
described in (1) to (24) mentioned above.

A compound or compounds of the invention are administered to a patient in need thereof in an effective amount to treat (therapeutically or prophylactically) vasomotor symptoms. An effective amount of a compound or compounds is dependent upon the extent of the symptoms, sex, age, body weight, administration mode and a salt type, variation in susceptibility to the drug, the specific type of the disease, and the like. The skilled artisan can readily determine and prescribe the effective amount of the compound or the salt or hydrate thereof, or a medicament, pharmaceutical composition, or selective estrogen receptor modulator required to treat, both therapeutically and prophylactically (reduce the likelihood of development), for example, to prevent, inhibit (fully or partially) or arrest the progress of vasomotor symptoms.

The SERM can be administered periodically, such as daily, every other day, weekly, etc. Additionally, a SERM in a controlled release form or formulation could be administered relatively infrequently, such as once a month. In general, for an adult, it is adequate to administer per day approximately 30 µg to 1000 mg, for example about 100 µg to 500 mg, such as 100 µg to 100 mg via an oral administration, and approximately 1 to 3000 µg/kg, for example 3 to 1000 µg/kg via injection, respectively, at once or divided into several times.

In a specific embodiment, a typical daily dose can be at least 1 mg/kg/day. For example, a typical daily dose can range from about 1 mg/kg/day to about 100 mg/kg/day, such as about 1 mg/kg/day to about 50 mg/kg/day, such as from about 1 mg/kg/day to about 10 mg/kg/day. In an even more specific embodiment, a typical daily dose can be about 1 mg/kg/day, about 2 mg/kg/day, about 3 mg/kg/day, about 4/mg/kd/day, about 5/mg/kd/day, about 6/mg/kd/day, about 7/mg/kd/day, about 8/mg/kd/day, about 9/mg/kd/day or about 10/mg/kd/day.

It is understood that the total dosage amount per day can be administered in a single dose or can be administered in multiple dosings such as twice, three or four or more times per day. The compounds for use in the methods of the invention can be formulated in unit dosage form. The term "unit dosage form" refers to physically discrete units suitable as unitary dosage for subjects undergoing treatment, with each unit containing a predetermined quantity of active material calculated to produce the desired therapeutic effect, optionally in association with a suitable pharmaceutical carrier. The unit dosage form can be for a single daily dose or one of multiple daily doses (e.g., about 1 to 4 or more times per day). When multiple daily doses are used, the unit dosage form can be the same or different for each dose. The compounds herein described can also be administered in conjunction with other currently used drugs to augment or supplement their therapeutic effects.

The compound according to the present invention or a salt thereof, or a hydrate thereof, can be formulated according to the conventional method. Examples of the preferred dosage forms include a tablet, a powder, a subtle granule, a granule, a coated tablet, a capsule, a syrup, a troche, an inhalant, a suppository, an injectable, an ointment, an ophthalmic ointment, an eye drop, a nasal drop, an ear drop, a cataplasm, a lotion and the like. In the formulation, generally used additives such as a diluent, a binder, an disintegrant, a lubricant, a colorant, a flavoring agent, and if necessary, a stabilizer, an emulsifyer, an absorption enhancer, a surfactant, a pH adjuster, an antiseptic, an antioxidant and the like can be used. In addition, the formulation is also carried out by combining compositions that are generally used as a raw material for pharmaceutical formulation, according to the conventional methods. Examples of these compositions (1) an oil such as a soybean oil, a beef tallow and synthetic glyceride; (2) hydrocarbon such as liquid paraffin, squalane and solid paraffin; (3) ester oil such as octyldodecyl myristic acid and isopropyl myristic acid; (4) higher alcohol such as cetostearyl alcohol and behenyl alcohol; (5) a silicon resin; (6) a silicon oil; (7) a surfactant such as polyoxyethylene fatty acid ester, sorbitan fatty acid ester, glycerin fatty acid ester, polyoxyethylene sorbitan fatty acid ester, a solid polyoxyethylene castor oil and polyoxyethylene polyoxypropylene block co-polymer; (8) water soluble macromolecule such as hydroxyethyl cellulose, polyacrylic acid, carboxyvinyl polymer, polyethyleneglycol, polyvinylpyrrolidone and methylcellulose; (9) lower alcohol such as ethanol and isopropanol; (10) multivalent alcohol such as glycerin, propyleneglycol, dipropyleneglycol and sorbitol; (11) a sugar such as glucose and cane sugar; (12) an inorganic powder such as anhydrous silicic acid, aluminum magnesium silicicate and aluminum silicate; (13) purified water, and the like.

Among the above-mentioned additives, 1) for instance, lactose, corn starch, sucrose, glucose, mannitol, sorbitol, crystalline cellulose and silicon dioxide as the diluent; 2) for instance, polyvinyl alcohol, polyvinyl ether, methyl cellulose, ethyl cellulose, gum arabic, tragacanth, gelatine, shellac, hydroxypropyl cellulose, hydroxypropylmethyl cellulose, polyvinylpyrrolidone, polypropylene glycol-poly oxyethylene-block co-polymer, meglumine, calcium citrate, dextrin, pectin and the like as the binder; 3) for instance, starch, agar, gelatine powder, crystalline cellulose, calcium carbonate, sodium bicarbonate, calcium citrate, dextrin, pectic, carboxymethylcellulose/calcium and the like as the disintegrant; 4) for instance, magnesium stearate, talc, polyethyleneglycol, silica, condensed plant oil and the like as the lubricant; 5) any colorants whose addition is pharmaceutically acceptable is adequate as the colorant; 6) for instance, cocoa powder, menthol, aromatizer, peppermint oil, cinnamon powder as the flavoring agent; 7) for instance, antioxidants whose addition is pharmaceutically accepted such as ascorbic acid and alpha-tophenol as the antioxidants, are used, respectively.

The term "pharmaceutically acceptable carrier" refers to a carrier that does not cause an allergic reaction or other untoward effect in patients to whom it is administered and are compatible with the other ingredients in the formulation. Pharmaceutically acceptable carriers include, for example, pharmaceutical diluents, excipients or carriers suitably selected with respect to the intended form of administration, and consistent with conventional pharmaceutical practices. For example, solid carriers/diluents include, but are not limited to, a gum, a starch (e.g., corn starch, pregelatinized starch), a sugar (e.g., lactose, mannitol, sucrose, dextrose), a cellulosic material (e.g., microcrystalline cellulose), an acrylate (e.g., polymethylacrylate), calcium carbonate, magnesium oxide, talc, or mixtures thereof. Pharmaceutically acceptable carriers may further comprise minor amounts of auxiliary substances such as wetting or emulsifying agents, preservatives or buffers, which enhance the shelf life or effectiveness of the therapeutic agent.

The compositions used in the methods of the present invention can be formulated as any one or more of the active compounds described herein and a physiologically acceptable carrier (also referred to as a pharmaceutically acceptable carrier or solution or diluent). Such carriers and solutions include pharmaceutically acceptable salts and solvates of compounds used in the methods of the instant invention, and mixtures comprising two or more of such compounds, pharmaceutically acceptable salts of the compounds and pharmaceutically acceptable solvates of the compounds. Such compositions are prepared in accordance with acceptable pharmaceutical procedures such as described in Remington's Pharmaceutical Sciences, 17th edition, ed. Alfonso R. Gennaro, Mack Publishing Company, Eaton, Pa. (1985).

When the compounds according to the present invention are obtained in a free form, they can be converted into a salt or a hydrate thereof by the conventional methods.

The term "salt" used herein is not limited as long as the salt is formed with the compound according to the present invention, and is pharmacologically acceptable; the preferred examples of the salt include a hydrohalide salt (for instance, hydrochloride, hydrobromide, hydroiodide and the like), an inorganic acid salt (for instance, sulfate, nitrate, perchlorate, phosphate, carbonate, bicarbonate and the like), an organic carboxylate salt (for instance, acetate salt, maleate salt, tartrate salt, fumarate salt, citrate salt and the like), an organic sulfonate salt (for instance, methanesulfonate salt, ethanesulfonate salt, benzenesulfonate salt, toluenesulfonate salt, camphorsulfonate salt and the like), an amino acid salt (for instance, aspartate salt, glutamate salt and the like), a quaternary ammonium salt, an alkaline metal salt (for instance, sodium salt, potassium salt and the like), an alkaline earth metal salt (magnesium salt, calcium salt and the like) and the like. In addition, hydrochloride salt, sulfate salt, methanesulfonate salt, acetate salt and the like are preferred as "pharmacologically acceptable salt" of the compounds according to the present invention.

Furthermore, when the compound according to the present invention may take various isomers (for instance, a geometric isomers, an optical isomer, a rotamer, a tautomer and the like), it can be purified by using the general separation means, for instance, recrystallization, optical resolution such as diastereomeric salt method, enzyme fractionation method, various chromatographies (for instance, thin layer chromatography, column chromatography, glass chromatography and the like) into a single isomer. The term "a single isomer" herein includes not only an isomer having a purity of 100%, but also an isomer containing an isomer other than the target, which exists even through the conventional purification operation. When using the compound according to the present invention as a raw material for a medicinal drug, the above-mentioned single isomer may be used, in addition, a mixture of isomers in any proportions may also be used.

A crystal polymorph sometimes exists for the compound according to the present invention, a salt thereof, or a hydrate thereof, and all crystal polymorphs thereof are included in the present invention. The crystal polymorph is sometimes single or sometimes a mixture, and both are included in the present invention.

Moreover, the present invention also includes the compounds still exhibiting the desired pharmacological activity even after the compound according to the present invention is metabolized in vivo such as by oxidation or hydrolysis.

In addition, the present invention also includes compounds that are metabolized in vivo such as by oxidation, reduction or hydrolysis to generate the compound according to the present invention, i.e., so-called prodrugs.

EXAMPLES

The invention is further described in the following examples.

Example 1

Treatment of Vasomotor Activity in a Rodent Model of Hot Flashes

The SERM, (R)-6-{2-{Ethyl[4-(2-ethylaminoethyl)benzyl]amino}-4-methoxyphenyl}-5,6,7,8-tetrahydronaphthalen-2-ol ("SERM A"), was evaluated for its ability to modulate vasomotor activity in a rodent model of hot flashes. (Merchenthaler, Maturitas, 1998 30:307-316). Briefly, ovariectomized adult rats were implanted with slow release morphine sulfate pellets on days 5 and 6 post-ovariectomy. Beginning at 4 days post-ovariectomy, once-daily treatment was initiated with a positive control, ethynyl estradiol (0.3 mg/kg), SERM A (1 and 10 mg/kg) or vehicle (95% corn oil, 5% DMSO by volume), delivered by subcutaneous injection. Treatment with the test agents was continued daily until the end of the study. On day 10, probes capable of continuously monitoring temperature were applied to the tail skin surface of the treated rats. The rats were then treated with naloxone, a morphine antagonist, and the change in skin temperature recorded for a period of 60 minutes.

The tail skin temperature change after administration of the antagonist, naloxone, are set forth in Table 1 and are shown in FIG. 1. As can be seen, the administration of the positive control, ethynyl estradiol, or 1 or 10 mg/kg of SERM A significantly reduced the increase in skin temperature after naloxone treatment, compared to rats administered vehicle alone. Statistical analysis shows no significant difference between the activity of the positive control, ethynyl estradiol, and SERM A on reducing tail skin temperature increase.

Additional doses of 0.1 and 0.01 mg/kg were also tested using the above described model, but did not significantly reduce the increase in skin temperature after naloxone treatment compared to rats administered vehicle alone.

TABLE 1

| | Vehicle | Ethynyl estradiol | SERM A | SERM A |
|---|---|---|---|---|
| Dose (mg/kg) | | 0.3 | 1 | 10 |
| Sample size | 7 | 7 | 9 | 10 |
| Mean Tail Skin Temp. | 5.6° C. | 1.2° C. | 2.1° C. | 2.0° C. |
| SD | 2.1° C. | 0.6° C. | 1.9° C. | 2.6° C. |
| p value vs. vehicle* | | 0.0002 | 0.004 | 0.009 |
| p value vs. estradiol* | | | 0.24 | 0.47 |

*$p < 0.05$ is significant

Example 2

Determination of Tissue Selectivity 19-day old Sprague-Dawley rats were treated with either vehicle (95% corn oil/5% DMSO), estradiol (0.01 mg/kg), raloxifene (10 mg/kg), tamoxifen (1 mg/kg) or SERM A (100, 30, 10, 3, 1, or 0.3 mg/kg). The rats were dosed once daily by subcutaneous injection for three consecutive days. 24 hours after the last dose, the rats were euthanized, uteri were harvested and their wet weight recorded.

The results of the above experiment are depicted in FIG. 2. As can be seen estradiol, raloxifene, and tamoxifen all significantly increased uterine weight relative to vehicle. The administration of SERM A did not result in any significant increase in uterine weight at any of the dosages tested.

Example 3

Antagonism of Estradiol-mediated Uterine Stimulation

19-day old Sprague-Dawley rats were treated with either vehicle (95% corn oil/5% DMSO), estradiol (0.01 mg/kg), or a combination of estradiol (0.01 mg/kg) and SERM A (10, 3, 1, 0.3, 0.1, 0.03, 0.01 mg/kg). The rats were dosed once daily by subcutaneous injection for three consecutive days. 24 hours after the last dose, the rats were euthanized, uteri were harvested and their wet weight recorded.

The results of the above experiment are illustrated in FIG. 3. As can be seen, estradiol alone significantly increases uterine weight compared to vehicle. The combination of SERM A and estradiol decreased the estradiol-mediated increase in a dosage dependent manner.

While this invention has been particularly shown and described with references to preferred embodiments thereof, it will be understood by those skilled in the art that various changes may be made therein without departing from the scope of the invention encompassed by the appended claims.

What is claimed is:

1. A method of treating vasomotor symptoms in a patient in need thereof comprising administering to said patient an effective amount of a selective estrogen receptor modulator represented by the following formula:

wherein
$R^{a\prime}$ and $R^{b\prime}$ independently are a hydrogen atom, a $C_1$-$C_8$ alkyl group which may have a substituent, or when $R^{a\prime}$ and $R^{b\prime}$ are bonded together, they may form, together with the nitrogen atom that is adjacent to $R^{a\prime}$ and $R^{b\prime}$, a 4- to 8 membered ring which may have a an additional heteroatom, and
$R^c$ is a hydrogen atom or a $C_1$-$C_6$ alkyl group; or a salt thereof, or a hydrate thereof.

2. The method of claim 1 wherein each of $R^a$ and $R^b$ represents a hydrogen atom, a methyl group, an ethyl group, a n-propyl group, an iso-propyl group, a n-butyl group, tent-butyl group, or a cyclohexyl group.

3. The method of claim 1 wherein the selective estrogen receptor modulator is a compound selected from the group consisting of:
   (a) (R)-6-{2-{Ethyl[4-(2-ethylaminoethyl)benzyl]amino}4-methoxyphenyl}-5,6,7,8-tetrahydronaphthalen-2-ol;
   (b) (R)-6-{2-{Ethyl[4-(2-methylaminoethyl)benzyl]amino]-4-methoxyphenyl}-5,6,7,8-tetrahydronaphthalen-2-ol;
   (c) (R)-6-{2-{Ethyl[4-(2-propylaminoethyl)benzyl]amino}-4-methoxyphenyl}-5,6,7,8-tetrahydronaphthalen-2-ol;
   (d) (R)-6-{2-{[4-(2-Butylaminoethyl)benzyl]ethylamino}-4-methoxyphenyl]-5,6,7,8-tetrahydronaphthalen-2-ol;
   (e) (R)-6-{2-Ethyl [4-(2-isopropylaminoethyl)benzyl]amino}-4-methoxyphenyl}-5,6,7,8-tetrahydronaphthalen-2-ol;
   (f) (R)-6-{2-{[4-(2-tert-Butylaminoethyl)benzyl]ethylamino}-4-methoxyphenyl}-5,6,7,8-tetrahydronaphthalen-2-ol; and
   (g) (R)-6- {2-{[4-(2-Cyclohexylaminoethyl)benzyl]ethylamino}-4-methoxyphenyl}-5,6,7,8-tetrahydronaphthalen-2-ol or a salt of any of the foregoing.

4. A method of treating vasomotor symptoms in a patient in need thereof comprising administering to said patient an effective amount of (R)-6-{2-{Ethyl[4-(2-ethylaminoethyl)benzyl]amino}-4-methoxyphenyl}-5,6,7,8-tetrahydronaphthalen-2-ol or a salt thereof.

5. A method of treating hot flashes in a female patient in need thereof comprising administering to said patient an effective amount of (R)-6-{2-{Ethyl[4-(2-ethylaminoethyl)benzyl]amino }-4-methoxyphenyl}-5,6,7,8-tetrahydronaphthalen-2-ol or a salt thereof.

6. The method of claim 4, wherein the vasomotor symptom is hot flashes or night sweats.

7. The method of claim 4 or claim 6, where the patient is a female.

* * * * *